US007665491B2

(12) United States Patent
Lampropoulos

(10) Patent No.: US 7,665,491 B2
(45) Date of Patent: *Feb. 23, 2010

(54) MULTI-PART WASTE CONTAINER APPARATUS

(75) Inventor: Fred P. Lampropoulos, SLC, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 377 days.

This patent is subject to a terminal disclaimer.

(21) Appl. No.: 11/434,289

(22) Filed: May 15, 2006

(65) Prior Publication Data

US 2007/0032764 A1 Feb. 8, 2007

Related U.S. Application Data

(63) Continuation-in-part of application No. 11/198,634, filed on Aug. 5, 2005, now Pat. No. 7,174,928.

(51) Int. Cl.
*B65B 1/04* (2006.01)

(52) U.S. Cl. ............ 141/311 A; 141/86; 604/110; 604/192; 206/366

(58) Field of Classification Search .......... 604/110, 604/192; 206/366, 370; 141/311 A, 86, 141/88, 98, 110
See application file for complete search history.

(56) References Cited

U.S. PATENT DOCUMENTS 4,572,374 A    2/1986   Sirotkin ............... 206/518

| | | | |
|---|---|---|---|
| 5,483,999 A | 1/1996 | Lampropoulos et al. ...... 141/86 |
| 5,707,173 A | 1/1998 | Cottone et al. .......... 405/129.55 |
| 6,053,314 A | 4/2000 | Pittman ................. 206/366 |
| 6,719,017 B1 | 4/2004 | McArthur ................ 141/86 |
| 6,783,003 B2 | 8/2004 | Simm ................... 206/366 |
| 7,174,928 B1 * | 2/2007 | Lampropoulos ........ 141/311 A |
| 2007/0029006 A1 | 2/2007 | Lampropoulos | |

FOREIGN PATENT DOCUMENTS

WO    WO 2007/019248    2/2007

OTHER PUBLICATIONS

International Search Report and Written Opinion, PCT/US06/30320, mailed Feb. 13, 2007, Fred P. Lampropoulos.
Notice of Allowance issued in U.S. Appl. No. 11/198,634, mailed Sep. 11, 2006, Fred P. Lampropoulos.
Supplemental Submission to Issue Fee Payment dated Dec. 11, 2006 in U.S. Appl. No. 11/198,634.
Issue Notification issued Jan. 24, 2007 in U.S. Appl. No. 11/198,634,.

* cited by examiner

*Primary Examiner*—Steven O Douglas
(74) *Attorney, Agent, or Firm*—Ryan D. Benson; Stoel Rives LLP

(57) ABSTRACT

A multi-part biowaste container configured to provide a low profile design while providing sufficient storage volume to accommodate the amount of blood, tissues, and other biological materials generated during a typical surgical procedure. The multi-part biowaste container includes an anti-splash container, a dual purpose lid container, and a supplemental container. The use of three separate container members increases the total volume and storage capacity of the biowaste containers while minimizing the overall profile or height of the containers.

34 Claims, 6 Drawing Sheets

MULTI-PART WASTE CONTAINER APPARATUS

CROSS-REFERENCE TO RELATED APPLICATIONS

The present application is a continuation-in-part of U.S. application Ser. No. 11/198,634 filed on Aug. 5, 2005, now U.S. Pat. No. 7,174,928 which is hereby incorporated by reference in its entirety.

BACKGROUND OF THE INVENTION

1. The Field of the Invention

The present invention relates to biowaste containers. In more particular, the present invention relates to a multipart biowaste container for use in a surgical setting.

2. The Relevant Technology

A great amount of attention has been focused on the appropriate disposition of blood, tissue, and other biological materials that are produced in modern surgical settings. Much of this focus results from concerns regarding contamination, possible infection, and exposure to such materials, as well as bioethical considerations directed to proper disposition of human tissues.

As a result, a number of basins and other specialized receptacles for blood, tissue, and other biological materials have been developed. Typically, during a medical procedure such blood, tissue, and biological materials are deposited into specially designed containers and/or receptacles until the completion of the procedures. After the completion of the procedure, the attending staff can then quickly and readily identify blood, tissues, and other biological materials that require special handling or special disposal procedures. The attending staff can then simply discard of the entire container without the need to separately attend to individual biowaste elements.

Some biowaste containers suffer from a number of deficiencies. For example, one problem presented by such biowaste containers is that they must be sufficiently large to accommodate the volume of biowaste that is typically produced during a typical surgical procedure. As a result, the biowaste containers must either have a fairly large footprint or have a sufficient depth to accommodate the required amount of biological waste.

Due to the fact that surgical working surfaces available to hold the biological waste container must also accommodate a number of other surgical implements, biological waste containers covering a large surface area are typically impractical. As a result, a biological waste container covering a smaller surface area but having a greater depth relative to their overall size are typically provided in such surgical settings. While biological waste containers having a greater height relative to their overall size are more practical due to surgical area surface constraints, such waste containers can be somewhat cumbersome to use. Additionally, the greater height can make it difficult to reach other tools or implements located close to the biological waste container. In some circumstances, attempts to access implements positioned adjacent the biological waste container can even result in tipping of the biological waste container when inadvertently bumped or contacted by a practitioner during surgery.

The size of such biological waste containers can also be fairly cumbersome to ship and store due their overall size. This can be particularly problematic where the biological waste container includes a lid or other secondary member. To alleviate this problem, the lids are sometimes shipped in place on the biological waste container. During preparation for surgery, the surgical staff simply removes the lid and places it to the side until the end of surgery. While this alleviates some of the problems with storage and shipping of the lid member, it can be inconvenient to find a place to store the lid during surgery. After the surgery is completed it can be difficult to locate the lid in order to place it on biological waste container for disposal.

Some biological waste container designs utilize a lid that nests on the underside of the biological waste container. During the procedure the lid remains in contact with the biological waste container until the procedure is completed. The lid can then be removed from the bottom of the biological waste container and placed over the top of the biological waste container to secure the contents of the biological waste container during disposal. Unfortunately, where the biological waste container becomes somewhat full of blood, tissue or other biological materials, removal of the lid from beneath the biological waste container can result in inadvertent spillage or other issuance of such materials from the biological waste container. As a result of the various complications and limitations of existing biological waste containers practitioners are forced to select biological waste containers having the least number of deficiencies for the type of procedure being performed. However, this can be impractical due to the purchasing constraints and storage realities inherent in hospital and surgical center economics.

BRIEF SUMMARY OF THE INVENTION

The present invention is directed to a multi-part biowaste container configured to provide a low profile design while providing sufficient storage volume to accommodate the amount of blood, tissues, and other biological materials generated during a typical surgical procedure. In one embodiment, the multi-part biowaste container includes an anti-splash container, a dual purpose lid container, and a supplemental container. The use of three separate container members increases the total volume and storage capacity of the biowaste containers while minimizing the overall profile or height of the containers.

To reduce the amount of surgical space occupied by three separate containers, the containers can be placed in various useful or convenient locations as needed during surgery. Because the containers have a relatively low profile relative to their overall size, the containers are not easily bumped or tipped during the procedure. According to one embodiment of the present invention, an adhesive pad is provided in connection with the bottom surface of one or more of the containers. The adhesive pad allows the containers to be adhered to the working surface to prevent inadvertent knocking or spilling of the container. This also allows the containers to be positioned in unconventional locations such as directly on the patient's chest or abdomen. Adhesive pads may be provided with each of the containers.

The anti-splash container includes a basin and a splash guard positioned to cover the basin. The basin is selected to have an overall surface area that corresponds to the surface area of biological waste containers typically used in a surgical setting. As previously discussed, the height of the wall of the basin is selected to provide an overall low profile to facilitate use of the container in a restricted surgical setting. The splash guard is provided to cover to the basin. The splash guard allows the introduction of fluid materials into the biological waste container in a manner which contains the fluids from inadvertent splashing or other release of the fluids once placed within the basin. According to one embodiment of the present invention, the splash guard includes a plurality of openings to provide access to the volume of the basin. For example, the splash guard according to one embodiment includes three splash guards. According to further embodiments, each opening may include one or more valves associated with one or more of the openings, such as silt valves, that allows for the introduction of blood, tissues or other biological materials into the basin in a safe and advantageous manner.

According to another embodiment of the present invention, an absorbent pad is provided in the bottom of the basin. The absorbent pad is configured to absorb blood, fluids, and other biological materials in a manner to facilitate containment of the biological materials in the basin. The absorbent pad can include chemical properties that solidify, or coagulate the biological materials such as in a gel form to maximize the containment of such materials.

The dual purpose lid container is provided as a secondary receptacle for receiving biological materials. The dual purpose lid container has overall dimensions that are similar to the anti-splash container. For example, the dual purpose lid container has a somewhat low profile while conforming to the overall footprint typically utilized biological waste containers. The dual purpose lid container includes a pour spout positioned at a corner of the upper rim of the dual purpose lid container. The pour spout allows for controlled and advantageous drainage of any excess blood, fluid, or biological materials from the dual purpose lid container into a secondary container.

Typically such blood, fluid, or other biological materials are drained from the dual purpose lid container into the slit valve of the anti-splash container. In this manner, all biological materials are consolidated in a manner allowing the containers to be easily and quickly be disposed of through proper procedures. Once the dual purpose lid container has been appropriately drained, the dual purpose lid container is configured to fit over the anti-splash container as a secondary and reliable containment mechanism. As a result, during disposal, the anti-splash container can be handled without leakage, splashing, or spilling of blood, fluids, or other materials from the anti-splash container.

According to one embodiment of the present said invention, an absorbent pad is also provided in connection with the dual purpose lid container. The absorbent pad performs essentially the same function as the absorbent pad of the anti-splash container. In this embodiment, the overall depth of the dual purpose lid container is designed such that when the absorbent pad of the dual purpose lid container is saturated with blood, fluid, or other materials, the saturated absorbent pad does not interfere with proper operation of the dual purpose lid container in covering and cooperatively engaging the anti-splash container. According to another embodiment of the present invention, the rim of the dual purpose lid container is slightly narrower than the rim of the anti-splash container. As a result, the rim of the dual purpose lid container is not inadvertently contacted and loosened relative to the anti-splash container. According to one embodiment, the total absorbent capacity of the biowaste container system is about 250 mL or greater.

The supplementary container is provided as a tertiary receptacle for biological materials in addition to the anti-splash container and the dual purpose lid container. The supplementary container also has dimensions similar to the anti-splash container and the dual purpose lid container. According to one embodiment of the present invention, the supplementary container is not only provided as a supplementary biowaste container, but may be utilized for other surgical purposes, such as a receptacle for saline or other flushing fluids. The supplementary container may also be utilized to hold surgical instruments, or gauze pads. The supplementary container can also be designed to provide a lid for the anti-splash container in the event that the volume of fluid in the dual purpose lid container is in excess of that which can be accommodated by the anti-splash container. According to one embodiment of the present invention, the dual purpose lid container and the supplementary container also utilize adhesive pads or other gripping surfaces to minimize slippage or tipping of these containers.

The dual purpose lid container and supplementary container are configured to nest beneath the anti-splash container during shipping. By having the ability to nest beneath the anti-splash container, the dual purpose lid container and supplementary container provide an overall low profile and efficient storage volume for the multipart biowaste container. This can substantially reduce the cost of packaging and storage of the multipart biowaste containers while facilitating preparation for the surgical procedure to be performed.

Once the multipart biowaste container is ready to be utilized in the surgical setting, the anti-splash container, dual purpose lid container, and supplementary container can be separated from one another. By utilizing three separate containers, the overall storage volume of the three containers is comparable to that of other biowaste containers without encumbering substantial amounts of the working surface or interfering with the use of other instruments and materials positioned on the working surface. According to one embodiment of the present invention, the height of the walls of one or more of the anti-splash container, the dual purpose lid container, and/or the supplementary container is less than two inches. According to another embodiment, when the anti-splash container, dual purpose lid container, the supplementary container are nested one within another, the height of the multipart biowaste container is less than three inches. According to another embodiment of the present invention, the anti-splash container, the dual purpose lid container, and the supplementary container have an individual wall height that is less than 1.5 inches and a total overall height when nested for shipping of less then 2 inches.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Reference will now be made to figures wherein like structures will be provided with like reference designations. It is understood that the drawings are diagrammatic and schematic representations of presently preferred embodiments of the invention, and are not limiting of the present invention nor are they necessarily drawn to scale.

Figure 1:
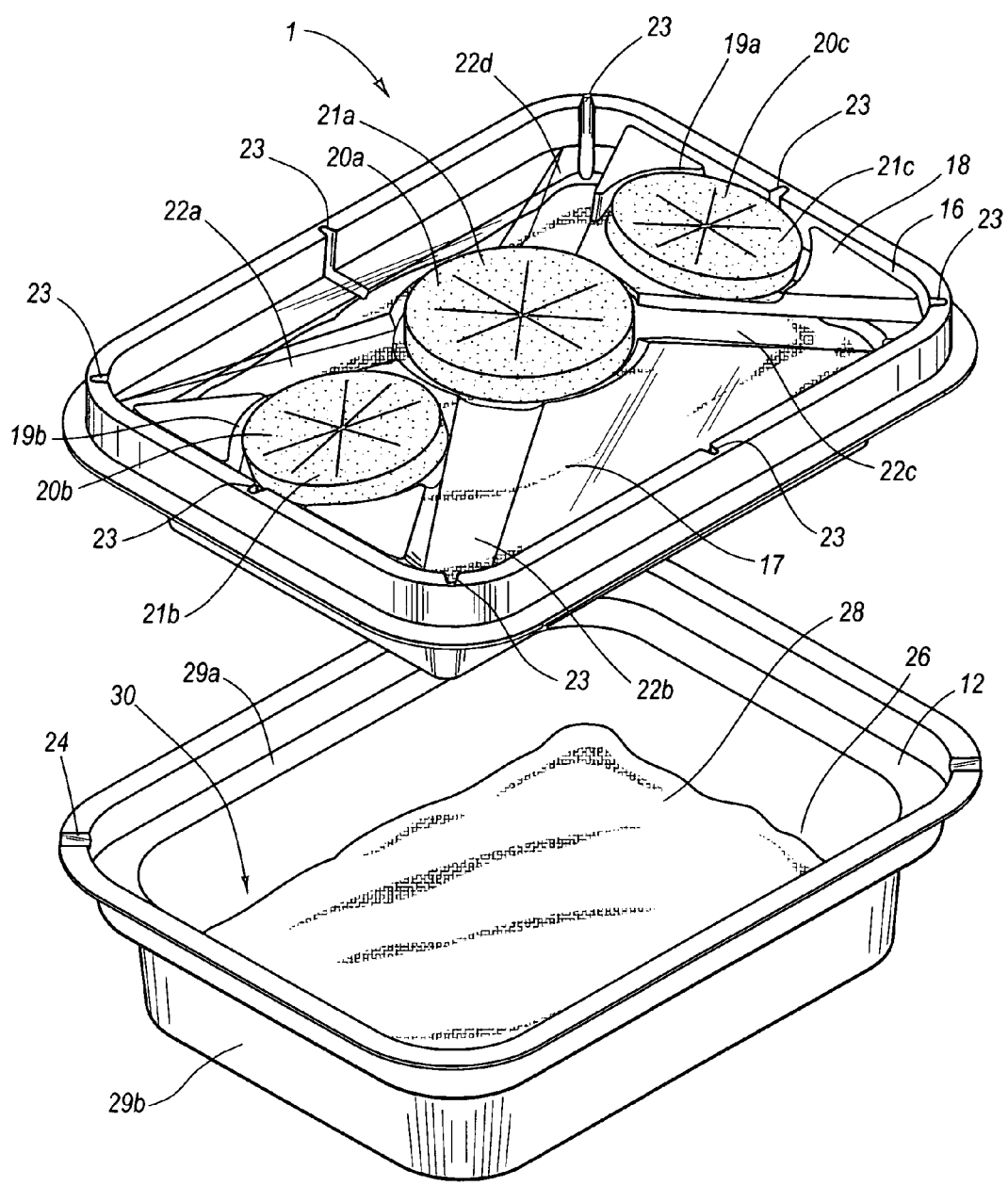
FIG. 1 is a perspective view of a biowaste container including an anti-splash container and a dual purpose lid.

FIG. 1 is a perspective view of a biowaste container according to one embodiment of the present invention. In the illustrated embodiment, biowaste container 1 comprises an anti-splash container 10 and a dual purpose lid 12. Anti-splash container 10 provides a receptacle for receiving fluids in a manner so as to prevent splashing of the fluids in a manner that may result in infectious or biological waste being splashed onto a practitioner. Dual purpose lid provides a secondary receptacle for receiving materials that may not be easily introduced into the anti-splash container such as blood falling from a catheter during exchange of guide wires, materials, and so forth. By providing both an anti-splash container 10 and a dual purpose lid 12 the total volume of fluid that can be contained within the combination of the anti-splash container 10 and the dual purpose lid 12 approximates the amount of volume that would be held within a much larger container. However, by utilizing more than one container within the biowaste container system 1, components of the biowaste container system 1 can be strategically located on the operating surface. Additionally, the total size of each individual container such as anti-splash container 10 and dual purpose lid 12 is much smaller preventing obstruction of the operating procedure that may lead to accidental bumping or tipping of the containers 10, 12.

In the illustrated embodiment, anti-splash container 10 comprises a basin 16 and a splash guard 18. Basin 16 provides a dish, or other volume containing mechanism within which fluids can be stored. The overall dimensions of basin 16 such as the width, length, and depth largely define the volume of biological waste that can be stored within basin 16. The splash guard 18 is positioned over the upper surface of basin 16. In the illustrated embodiment, the inward facing lip on the upper rim of basin 16 allows for the retention of splash guard 18 in position over basin 16. In the illustrated embodiment, an absorbent pad 17 is depicted being positioned within basin 16. Absorbent pad 17 is configured to absorb blood or other fluid-type materials which are positioned within anti-splash container 10 to minimize leakage or spillage of such fluids from the anti-splash container.

In the illustrated embodiment, splash guard 18 includes input sites 20a, b, c, slit valves 21a, b, c, flow channels 22a, b, c, d, and channeling ridges 19a, b. Input sites 20a, b, c are positioned along the ridge of splash guard 18. A first input site 20a is positioned on the center upper portion of splash guard 18. Input sites 20b and c are positioned on alternating angular and outward facing surfaces of the splash guard 18. Input sites 20a, b, c are configured to allow the introduction of biological waste through the splash guard and into the interior of basin 16. In the illustrated embodiment, slit valves 21A, B, C are utilized in connection with input sites 20a, b, c. In the illustrated embodiment, slit valves 20a, b, c comprise foam members which have one or more slits positioned in the surface thereof. In this manner, a syringe or a similar instrument can be positioned through the slits of slit valves 21a, b, c in a manner so as to further prevent splashing of fluids while also allowing sufficient deformation and resilience to allow for the introduction of different sized syringes or other instruments.

Splash guard 18 also includes a number of relief surfaces which facilitate drainage of fluids or other biological waste into the basin 16. In the illustrated embodiment, each of the four angular outward facing surfaces of splash guard 18 is slanted toward the outer rim of basin 16. In this manner, in the event that blood or other fluids inadvertently contact the outer surface of the splash guard instead of being introduced into the basin 16, such blood or other fluids will flow along the surface of splash guard 18 and toward the rim of anti-splash container 10. The rim of anti-splash container 10 extends an amount in a vertical direction above the outer rim of splash guard 18 so as to catch such fluids or liquids flowing along the surface of splash guard 18. Additionally, the rim of basin 16 includes a plurality of vent channels 23. Vent channels 23 allow for the passage of blood or other fluids from the upper surface of splash guard 18 to the interior of basin 16. In the illustrated embodiment, vent channels 23 do not extend through the entire upper portion of the rim of basin 16. Instead, they are only positioned on the inward portion of the upper surface of the rim of basin 16. In this manner, vent channels 23 do not allow for the passage of fluids to the exterior of the biowaste container system 1 when dual purpose lid 12 is positioned over anti-splash container 10 in a lid-like fashion.

A plurality of flow channels 22a, b, c, d are also positioned in the upper surface of splash guard 18. Flow channels 22a, b, c, d also facilitate the channeling of fluid or materials toward vent channels 23 positioned in the corners of the basin 16. Flow channels 22a, b, c comprise curved channels which extend from input site 20a to the outer rim of basin 16. Flow channels 22a, b, c, d also extend an amount below adjacent surfaces of the splash guard 18. Channeling ridges 19a and b are also illustrated. Channeling ridges 19a and b are positioned adjacent input sites 20b, c. Channeling ridges 19a, b extend an amount upward where an elevation higher than input sites 20b, c so as to channel fluids into input sites 20b, c or the corresponding vent channels 23.

The absorbent pad 17 may occupy a portion of the surface of the basin 16 of the anti-splash container 10 below at least one of the input sites 20a, b, c. According to the illustrated embodiment, the absorbent pad 17 occupies a portion of the surface of the basin 16 of the anti-splash container below all of the input sites 20a, b, c. Thus, a portion of liquid introduced into the anti-splash container through any of the input sites 20a, b, c will be absorbed by the absorbent pad 17.

In the illustrated embodiment, a dual purpose lid 12 is also shown. Dual purpose lid 12 includes a pour spout 24, a basin 26, an absorbent pad 28, an inside surface of a multi-part wall 29a, an outside surface of a multi-part wall 29b, and a bottom surface 30. Basin 26 is configured to receive the volume of fluid which is positioned within dual purpose lid 12. Dual purpose lid does not include a splash guard so as to facilitate introduction of larger biological waste or for the utilization of different instruments that may not be as easily utilized in the context of a splash guard 18. In the illustrated embodiment, a pour spout 24 is positioned in a corner of dual purpose lid 12. Pour spout 24 facilitates the channeling of fluid from basin 26 of dual purpose lid into one or more of the input sites of anti-splash container 10. In the illustrated embodiment, pour spout 24 does not extend beyond the outer rim of dual purpose lid 12. In this manner, the pour spout 24 does not inadvertently puncture or damage the sterile packaging within which the biowaste container system 1 is packaged. Additionally, in the event that the user is utilizing dual purpose lid 12 in a sealed and lid-like fashion over anti-splash container 10, the user may not inadvertently grasp the pour spout 24 to lift the dual purpose lid 12 off of the anti-splash container 10 and inadvertently allow for spilling of the fluids or materials positioned therein.

In the illustrated embodiment, an absorbent pad 28 is depicted. Absorbent pad 28 is utilized to absorb fluid, liquids, or other biological waste positioned within the dual purpose lid 12. In this manner, inadvertent spilling of such blood, fluid, or the like is minimized. This can be particularly helpful, in the event that a large amount of fluid is positioned within dual purpose lid 12. Where a large amount of fluid is positioned within dual purpose lid, a portion of that fluid can be absorbed with an absorbent pad 28. Any remaining fluid can be introduced into anti-splash container 10 in connection with pour spout 24.

Dual purpose lid 12 can then be snapped in a lid-like fashion over anti-splash container effectively sealing all materials within the biowaste container system 1. In the illustrated embodiment, inside surface of multi-part wall 29*a* and outside surface of multi-part wall 29*b* have a height which is greater than one inch. In this manner, the total volume of liquid or other material that can be held within dual purpose lid can be sufficient to contain a volume of fluid that may result from different types of procedures being utilized. For example, during a femoral artery catheter exchange procedure, a substantial amount of liquid such as blood, serum, or the like may be generated. In this manner, all such fluid can be contained within a single container such as the dual purpose lid 12. In the illustrated embodiment, a secondary pour spout is also positioned in the opposite corner of the rim of the dual purpose lid 12. This allows the practitioner to quickly pour the contents of the fluid from dual purpose lid into the anti-splash container without needing to substantially reposition the dual purpose lid 12. In the illustrated embodiment, the rim of dual purpose lid is also somewhat smaller than the rim of anti-splash container. This minimizes the risk that a practitioner may inadvertently grasp the rim of dual purpose lid 12 and remove or loosen the dual purpose lid 12 from its sealed positioning over anti-splash container 10.

As previously introduced, an absorbent pad 17 is also associated with the anti-splash container 10. The combination of absorbent pad 17 with the anti-splash container 10 and the absorbent pad 28 with the dual purpose lid provide the biowaste container system 1 with a large absorbent capacity. The absorbent capacity of the biowaste container system 1 may refer generally to the amount of fluid retained absorbed and retained by each absorbent pad 17, 28. According to one embodiment, the combined absorbent capacity of the absorbent pads 17, 28 may be about 250 mL of fluid or larger. Further, according to one embodiment, one or both of the absorbent pads 17, 28 can optionally include sodium polyacrylate.

Figure 2:
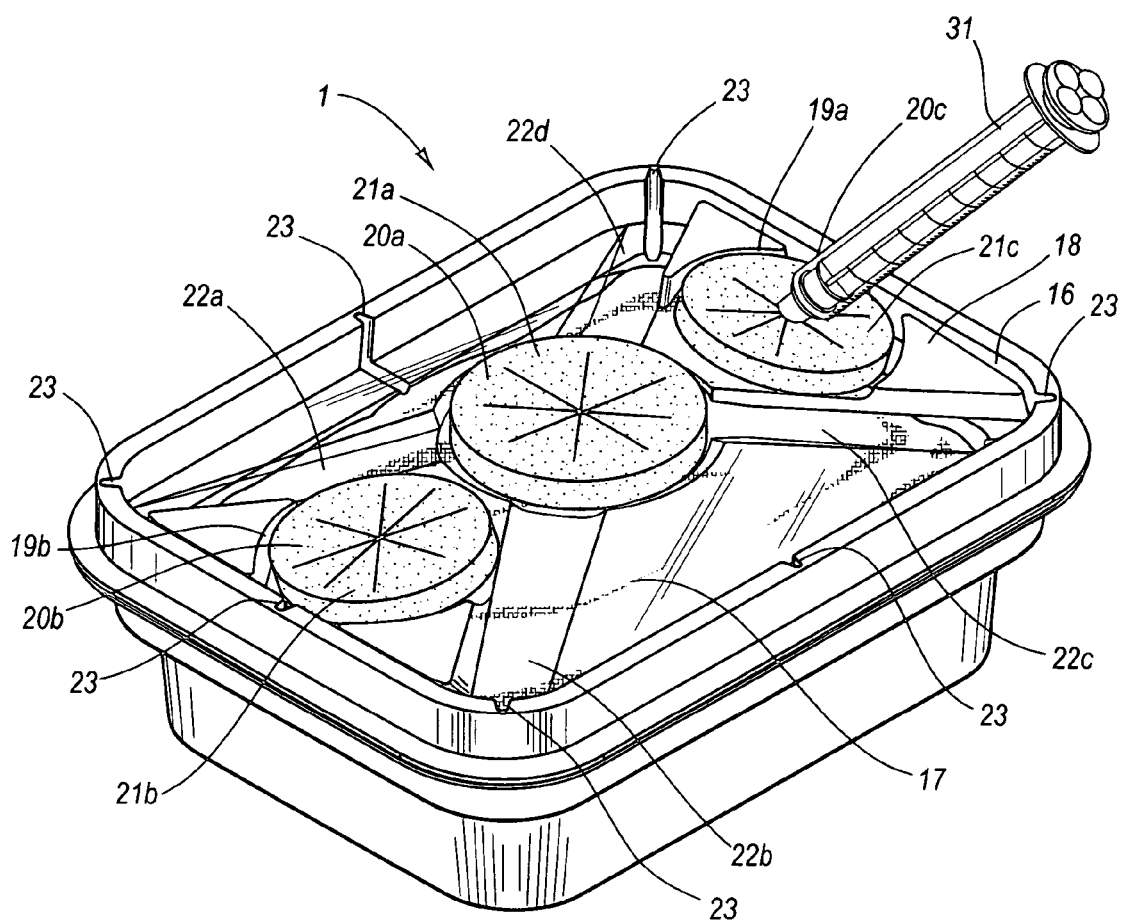
FIG. 2 illustrates a biowaste container in which fluid from a syringe is being injected into the anti-splash container.

FIG. 2 is a perspective view of a biowaste container system 1 depicting the introduction of biological fluid such as blood into an anti-splash container 10. In the illustrated embodiment, a syringe 31 is being positioned through a slit valve 21*c*. Materials within syringe 31 can comprise blood, medicines, fluids, or other materials that can potentially be contaminated. The practitioner can simply insert the tip of syringe 31 through the input site 20*c* and optionally through a slit valve 21*c* and forcefully eject the contents of syringe 31 into the anti-splash container 10. Any splashing of such fluids from syringe 31 is effectively contained by splash guard 18. In this manner, the practitioner need not be concerned with slowly ejecting such fluid and can move to other potentially more urgent and/or time sensitive matters. Additionally, in the event that some of the fluids leak onto the exterior surface of splash guard 18, such fluids will carefully be caught by one of the relief surfaces such as channel ridges 19*a, b*, or flow channels 22*a, b, c, d*. Additionally, the positioning of multiple input sites facilitates more advantageous positioning of the syringe as desired by the particular procedure being performed, or other convenience or access type issues that can arise during a surgical procedure having a certain degree of complexity.

Figure 3:
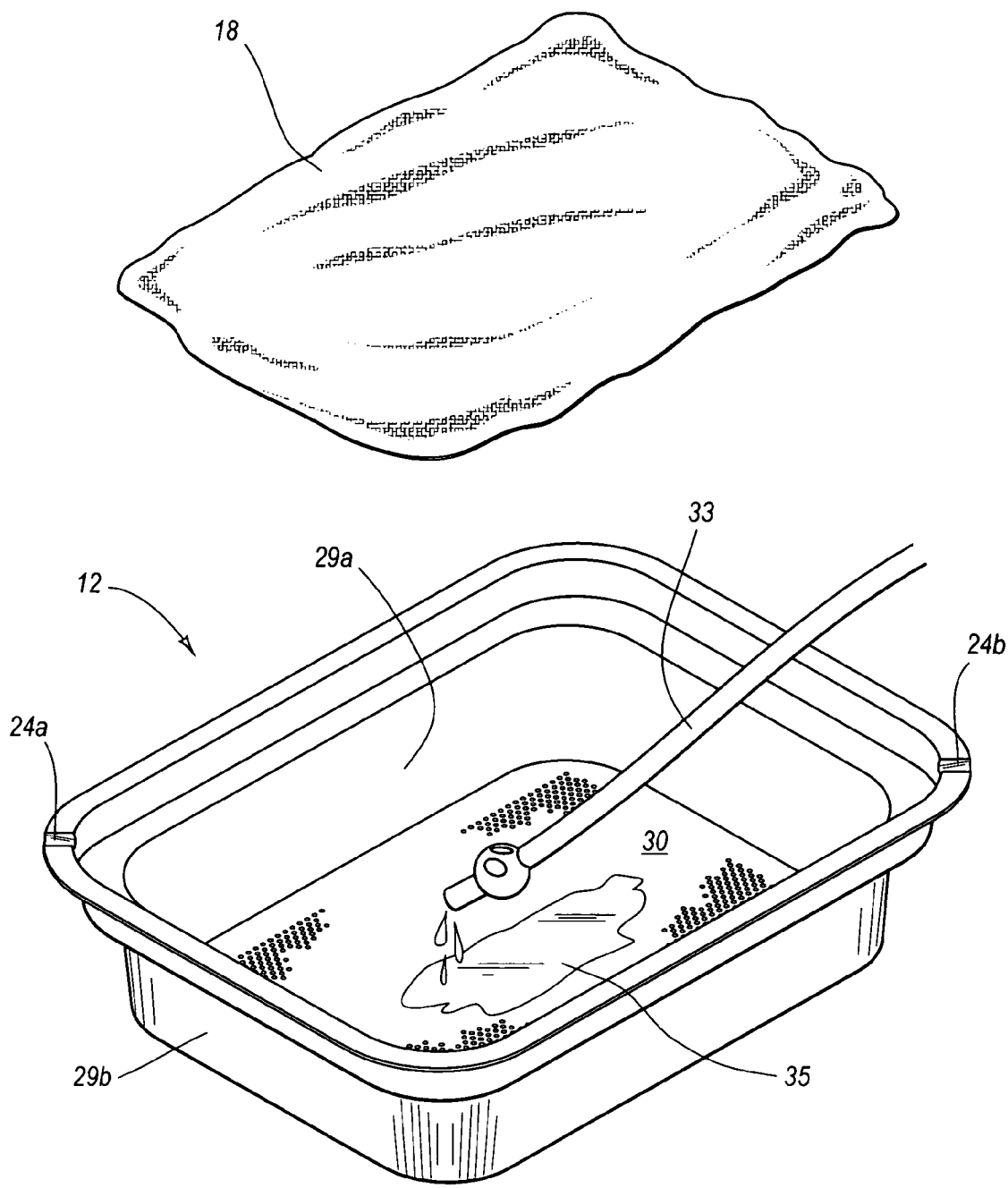
FIG. 3 is a perspective view of a dual purpose lid being utilized with a catheter during a catherization exchange procedure.
Figure 4:
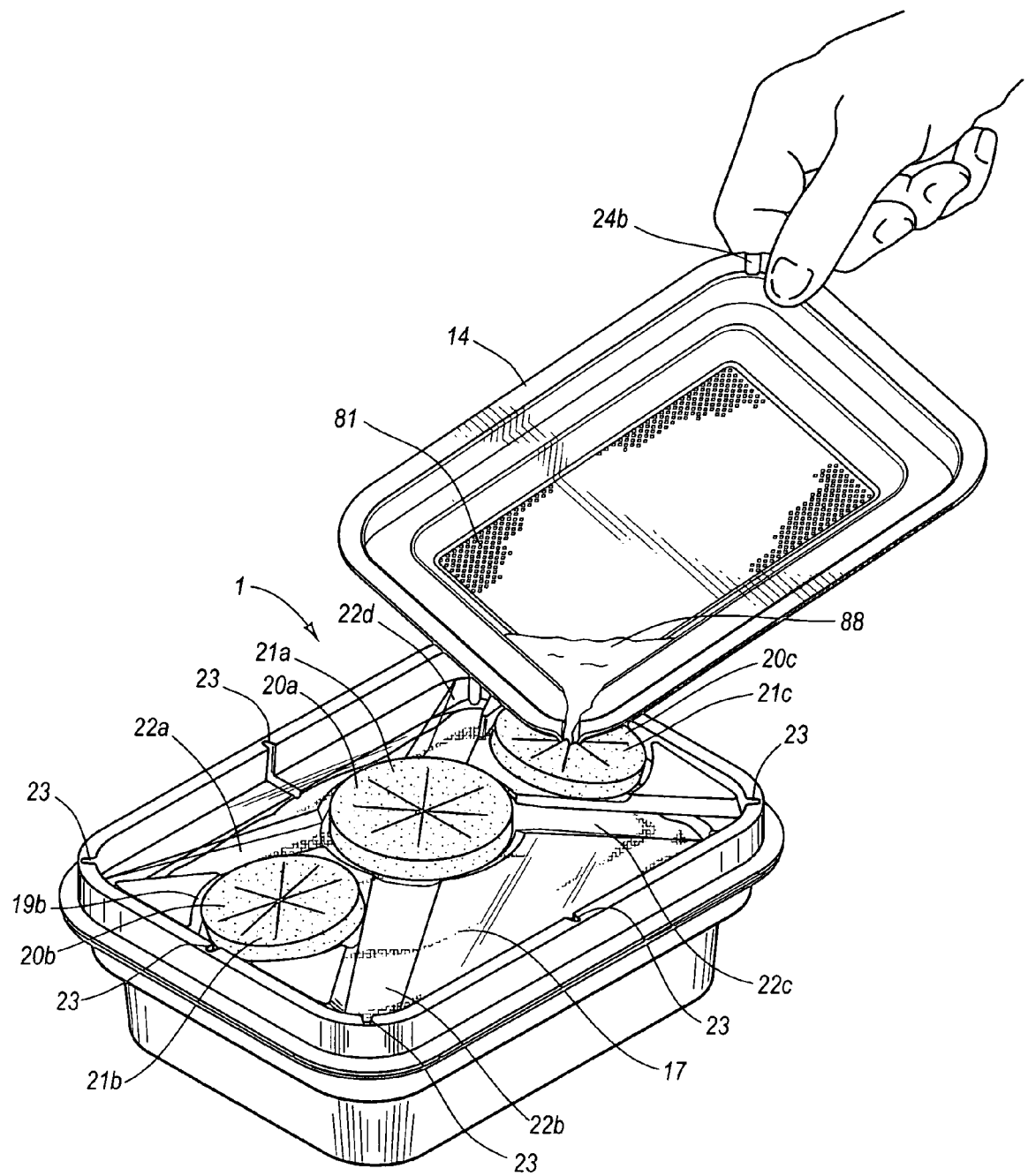
FIG. 4 is a perspective view of a biowaste container in which fluid from a dual purpose lid is being poured into the anti-splash container.

FIG. 3 is a perspective view of a dual purpose lid 12 being utilized during the course of the procedure. In the illustrated embodiment, a catheter 33 is being utilized with a dual purpose lid 12. During many catheterization procedures, multiple components utilized with a catheter may need to be withdrawn and exchanged during the course of the procedure. For example, an introducer sheathe, guide wire, medicine, fluid, or the like may need to be exchanged during the course of the procedure. Having an open container such as dual purpose lid 12 allows for such a procedure to be performed while capturing any blood, or other fluid which is expelled from the proximal end of the catheter during the course of the procedure. In the illustrated embodiment, an absorbent pad 18 is shown separated from the dual purpose lid 12. As will be appreciated by those skilled in the art, the absorbent pad is typically positioned within the dual purpose lid to absorb any materials such as blood, liquid, or the like which are introduced into the dual purpose lid 12. Absorbent pad 18 is shown separated from the dual purpose lid simply for the sake of clarity and to illustrate the general context of an absorbent pad within the dual purpose lid 12. As was previously discussed, such absorbent pads can comprise any absorbent material such as a sodium polyacrylate. Also as previously introduced, sodium polyacrylate and other absorbent pads can optionally provide an absorbent volume of up to 125 ml or more each. As a result, a fairly substantial volume of fluid can be absorbed within the dual purpose lid 12 without detracting from the ability of that lid to be positioned in a lid-like fashion over anti-splash container 10. In the illustrated embodiment, a volume of fluid 35 is shown within dual purpose lid 12. In the illustrated embodiment, a first pour spout 24*a* is positioned in one corner of a dual purpose lid 12 and a secondary pour spout 24*b* is positioned in the other corner of dual purpose lid. As previously discussed, the use of first and second pour spouts provides a degree of convenience in the event that the practitioner desires to drain the contents of the dual purpose lid into anti-splash container 10. According to one embodiment a of the present invention, a tertiary container is provided. In this embodiment as shown in FIG. 4, supplementary container 14 can be utilized in the absence of an absorbent pad. The supplementary container 14 can provide yet another receptacle for receiving fluids or other material utilized during the course of a procedure. For example, supplementary container 14 can be utilized to hold gauze squares or other material which are utilized during the course of the procedure. According to one embodiment of the present invention, the bottom surface 30 includes a textured knurling. The textured knurling can provide one or both of an anti-slip friction texturing on the underside of the lid and/or an anti-slip friction texture on the inside surface of the supplementary container 14. The anti-slip friction surface on the interior surface of the supplementary container 14 can minimize the slippage of materials that are positioned within the supplementary container.

Supplementary container 14 includes a volume of fluid 88 positioned therein. The volume of fluid is being poured through a pour spout 24a and into an introduction site of the splash guard 18 of anti-splash container 10. In the illustrated embodiment, a reverse knurling 81 is also positioned in the inward bottom surface of the supplementary container 14. As previously discussed, a reverse knurling 81 minimized the slippage of gauze squares or other materials positioned within supplementary container 14. The positioning of input sites 20a, b, c facilitates the flow of fluids from the supplementary container 14 and into the basin 16.

In the illustrated embodiment, the dual purpose lid 12 is positioned on the underside of anti-splash container 10. This may be due to a number of factors. For example, the type of procedure being performed may not have required the use of a dual purpose lid container. In this context, the supplementary container 14 can also be positioned in a fluid-tight lid configuration over the surface of anti-splash container 10. According to one embodiment of the present invention, the supplementary container 14 does not include pour channels 24a and 24B as are depicted in the current embodiment. Instead, the entire rim of the supplementary container has a substantially uniform configuration. According to another embodiment of the present invention, the depth of the pour spouts 24a, 24b are somewhat reduced such that when the supplementary container 14 or dual purpose lid 12 are positioned in a lid-like fashion over the anti-splash container 10, such that the pour spout 24 does not provide a channel for leakage of fluid from the interior of the anti-splash container 10 and the corresponding lid.

Figure 5:
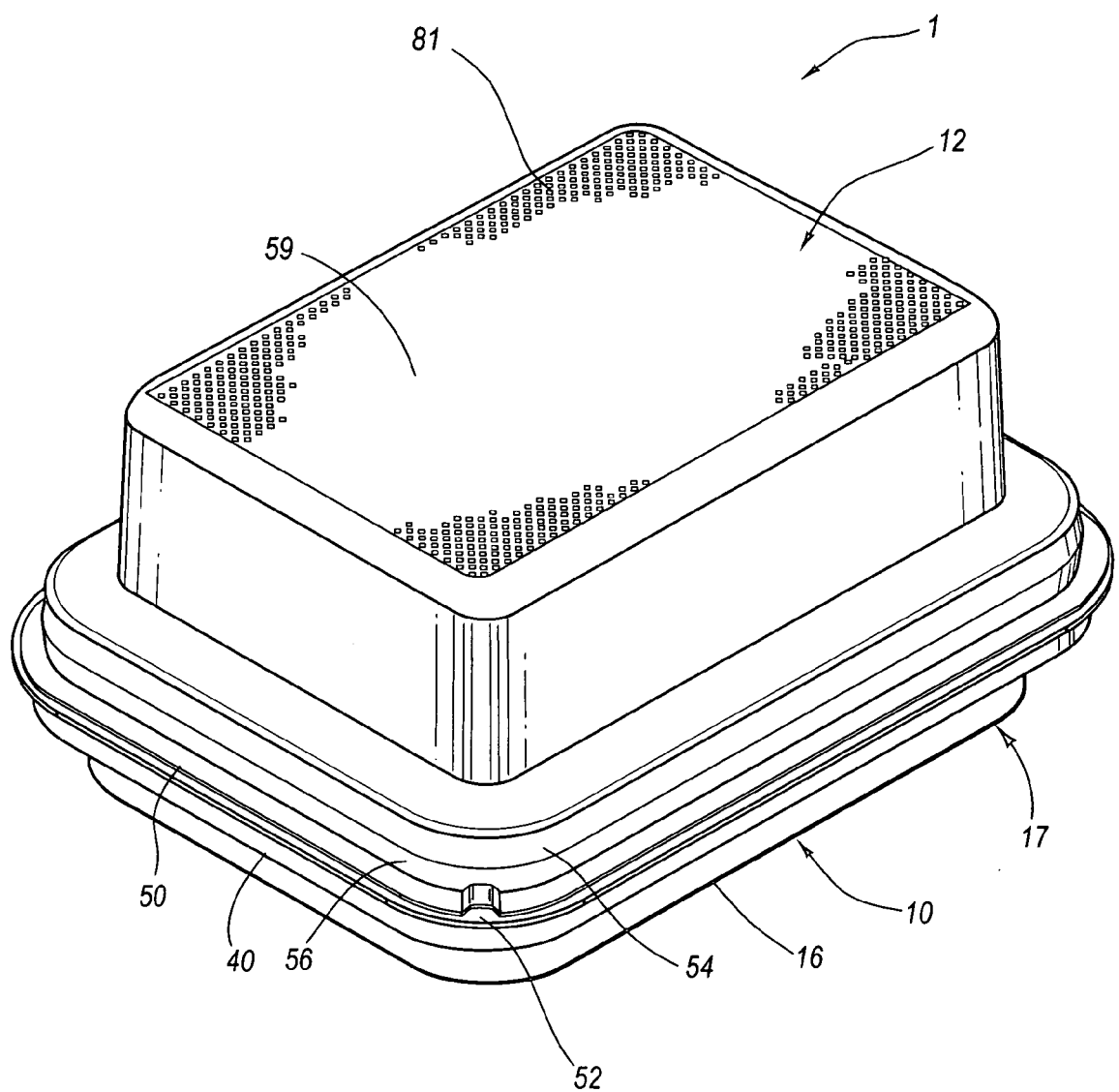
FIG. 5 is a perspective view of a biowaste container in which dual purpose lid has been positioned in fluid-tight configuration over the anti-splash container.

FIG. 5 is a perspective view of a biowaste container system 1 in which a dual purpose lid 12 is positioned in a lid-like configuration over an anti-splash container 10. In the illustrated embodiment, anti-splash container 10 includes a multi-part wall 17. Multi-part wall 17 includes an extension rim 40. In the illustrated embodiment, dual purpose lid 12 also includes an extension rim 50. Additionally, dual purpose lid 12 includes a first upper angular surface 52, a second upper angular surface 54 and an inner rim 56. Extension rim 50 of dual purpose lid 12 is somewhat shorter or narrower than extension rim 40 of anti-splash container 10. This is due to the fact that once the dual purpose lid 12 has been positioned in a lid-like fashion over anti-splash container 10, the inadvertent removal of dual purpose lid 12 is minimized by the difficulty of grasping or inadvertently contacting the extension rim 50 of the dual purpose lid 12. According to one embodiment of the present invention, the width of the extension rim 50 of the dual purpose lid and the width of the extension rim 40 of the anti-splash container 10 are configured to terminate approximately in the same location.

In the illustrated embodiment, first upper angular surface 52, second upper angular surface 54 and inner rim 56 are utilized to facilitate a seal between dual purpose lid 12 and anti-splash container 10. According to one embodiment of the present invention, first upper angular surface 52 substantially contacts a corresponding angular surface of anti-splash container 10. Second upper angular surface 54 substantially contacts with corresponding angular surface of anti-splash container 10. Inner rim 56 extends inwardly sufficient to contact the upper contact surface of the rim of basin 16. In this manner, a plurality of contact surfaces are provided on both anti-splash container and dual purpose lid to maximize contact on the sealing surfaces of anti-splash container 10 and dual purpose lid 12. Maximizing contact between multiple surfaces creates a more tortuous path for fluid to travel when the dual purpose lid 12 is coupled to the anti-splash container 10. A more tortuous path may decrease the likelihood that fluid will thus escape.

According to one embodiment of the present invention, a fluid-tight fitting is provided between anti-splash container 10 and dual purpose lid 12.

According to another embodiment of the present invention, the actual circumference of the lid of dual purpose lid container is configured to provide a compression fitting with the rim of anti-splash container 10. In particular, according to one embodiment, one or more features of the rim of the dual purpose lid 12 may be slightly narrower than corresponding features on the outer perimeter of the rim of the anti-splash container 10. As a result, when such a feature of the dual purpose lid 12 is urged into contact with a corresponding feature on the anti-splash container 10, that feature on the anti-splash container 10 is compressed, the feature on the dual purpose lid 12 is expanded, or both. In either case, the two features are held together in compression. The compression may be sufficient to reduce or prevent leakage of fluid from within the assembled anti-splash container 10 and the dual purpose lid 12.

According to one embodiment of the present invention, the dual purpose lid 12 is configured to remain in place over the anti-splash container 10 such that the entire biowaste container system 1 can be disposed of together.

According to one embodiment of the present invention, the fitting between the dual purpose lid 12 and the anti-splash container 10 is sufficiently tight that a casual attempt to remove the dual purpose lid 12 is not possible without some extraordinary or measured approach to removal of the lid.

Figure 6:
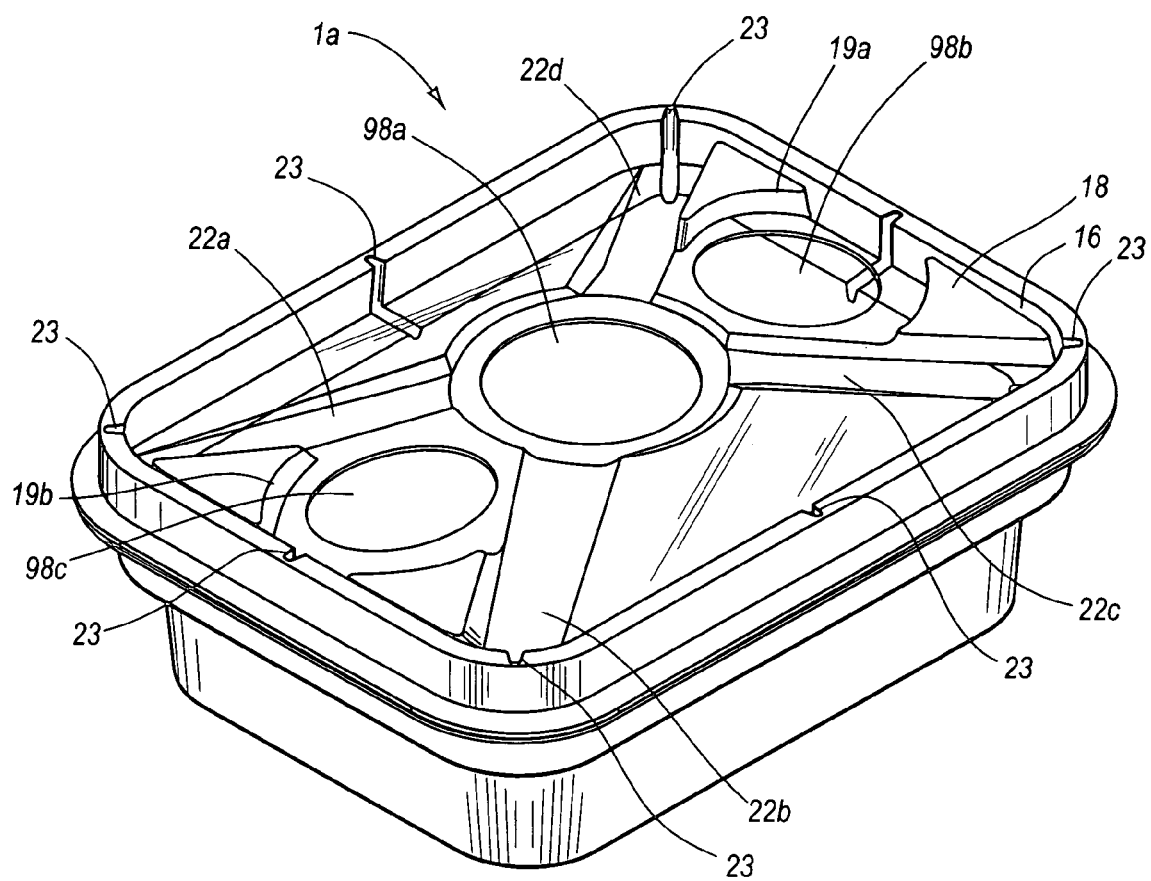
FIG. 6 is a perspective view of an anti-splash container according to an alternative embodiment of the present invention.

FIG. 6 is a perspective view of a biowaste container system 1a according to an alternative embodiment of the present invention. In the illustrated embodiment, an anti-splash container 10 includes a splash guard 18. Splash guard 18 includes input sites 98A, B, C. Input sites 98a, b, c do not include a slit valve as illustrated in FIGS. 1 through 5. Instead, input sites 98a, b, c are open to the internal portion of anti-splash container 10. In this manner, a user can simply insert an implement, instrument, or other tool for the injection of fluids, biowaste material or the like into the internal portion of the anti-splash container 10. In the illustrated embodiment, a tapered surface is positioned around the outer rim of input sites 98a, b, c. In this manner, inadvertent dripping, splashing around the exterior of input sites 98a, b, c results in the flow of material into the internal portion of the anti-splash container 10. Additionally, the tapered surface or channel configuration of the portion of the splash guard 18 surrounding input sites 98a, b, c facilitates the directioning or channeling of the syringe, tool, or other implement into the input site. In this manner, the practitioner is not required to precisely position such tool or implement, but can pay attention to other portions of the procedure to be performed.

The present invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A multipart biowaste container system configured to provide a low profile design while providing sufficient storage volume to accommodate the amount of blood, tissues, and other biological materials generated during a typical surgical procedure, the multipart biowaste container comprising:
   a first biowaste container adapted to accommodate blood, fluids, and other biological waste material, the first biowaste container comprising:

a basin for holding the blood, fluids, and other biological material introduced into the first biowaste container; and a cover positioned over the basin to minimize splashing or spilling of materials positioned in the basin while providing a plurality of openings to allow passage of blood, fluids, and other biological materials through the cover into the basin; and a second biowaste container adapted to accommodate blood, fluids, and other biological waste material, the second biowaste container comprising:

a basin adapted to accommodate the blood, fluids, and other biological waste material introduced into the second biowaste container, the basin having a multipart wall adapted to nest with the basin of the first biowaste container during shipping and storage of the multipart biowaste container while also being adapted to be secured in a lid configuration to the first biowaste container to retain the materials in the first biowaste container during disposal.

2. The multipart biowaste container of claim 1, further comprising a third biowaste container configured to nest with one or both of the first biowaste container and the second biowaste container.

3. The multipart biowaste container of claim 2, wherein the third biowaste container is adapted to be secured to at least one of the first biowaste container and the second biowaste container in a lid configuration.

4. The multipart biowaste container of claim 1, wherein the cover of the first biowaste container comprises a splash guard.

5. The multipart biowaste container of claim 4, wherein the cover includes at least one valve associated with at least one of the openings to facilitate passage of blood, fluids, and other material into the basin while minimizing splashing of such materials.

6. The multipart biowaste container of claim 1, further comprising at least one absorbent member positioned within the basin of at least one of the first and second biowaste container to retain blood, fluids, and other biological waste material.

7. The multipart biowaste container of claim 6, wherein at least one absorbent member is positioned within the basin of each of the first and second biowaste containers, the absorbent members having a total absorbent capacity of about 250 mL or greater.

8. The multipart biowaste container of claim 7, wherein at least one of the absorbent members includes sodium polyacrylate.

9. The multipart biowaste container of claim 1, wherein the height of the multipart wall of the second biowaste container minimizes contact between the absorbent member of the second biowaste container and the cover of the first biowaste container when the second biowaste container is secured to the first biowaste container in a lid configuration.

10. The multipart biowaste container of claim 1, the cover positioned over the basin to minimize splashing or spilling of materials positioned in the basin including three openings to allow passage of blood, fluids, and other biological materials through the cover into the basin.

11. A multipart biowaste container system configured to provide a low profile design while providing sufficient storage volume to accommodate the amount of blood, tissues, and other biological materials generated during a typical surgical procedure, the multipart biowaste container comprising:

a first biowaste container to accommodate blood, fluids, and other biological waste material, the first biowaste container having a length of at least 3.5 inches, a width of at least 2.5 inches, and a height of no more than 2.0 inches having a plurality of openings adapted; and one or more secondary biowaste containers adapted to accommodate blood, fluids, and other biological waste material, the one or more secondary biowaste containers having a length of at least 3.5 inches, a width of at least 2.5 inches, and a height of no more than 2.0 inches, wherein at least one of the one or more secondary biowaste containers is configured to be secured to the first biowaste container in a lid fashion to retain the contents of the first biowaste container during disposal, and wherein the first biowaste container and the secondary biowaste containers are configured to nest with one another to minimize the size of the multipart biowaste container system during shipping and storage and when the first biowaste container and the one or more secondary biowaste containers are separated from one another, the containers being configured to provide sufficient storage volume to provide an absorbent capacity of about 250 mL or more.

12. The multipart biowaste container of claim 11, wherein the first biowaste container comprises an anti-splash container and an absorbent member.

13. The multipart biowaste container of claim 11, wherein at least one of the one or more secondary biowaste containers comprise a dual purpose lid container.

14. The multipart biowaste container of claim 11, wherein at least one of the one or more secondary biowaste containers comprise a supplementary container having reverse knurling on an inward bottom surface of the supplementary container.

15. The multipart biowaste container of claim 11, wherein at least one of the first biowaste container and the one or more secondary biowaste containers have a length of at least four inches, a width of at least three inches and a height of no more than 1.5 inches.

16. The multipart biowaste container of claim 11, wherein the first biowaste containers and the one or more secondary biowaste containers have a total overall height when nested for shipping of less than 2 inches.

17. The multipart biowaste container of claim 11, wherein the first biowaste includes a cover adapted to minimize splashing or spilling of the contents of the multipart biowaste container.

18. The multipart biowaste container of claim 17, further comprising one or more vent channels in connection with the cover, the vent channels being defined in an interior of the perimeter of the cover.

19. The multipart biowaste container of claim 18, wherein the one or more vent channels minimize the flow of fluid to an exterior of the perimeter of the cover.

20. The multipart biowaste container of claim 17, wherein the cover comprises one or more flow channels to facilitate passage of blood, fluids, or other materials from the outside surface of the cover to the interior of the biowaste container.

21. A multipart biowaste container system configured to provide a low profile design while providing sufficient storage volume to accommodate the amount of blood, tissues, and other biological materials generated during a typical surgical procedure, the multipart biowaste container comprising:

a first biowaste container adapted to accommodate blood, fluids, and other biological waste material, the first biowaste container comprising:

a basin for holding the blood, fluids, and other biological material introduced into the first biowaste container;

a cover positioned over the basin to minimize splashing or spilling of materials positioned in the basin while providing three openings to allow passage of blood, fluids, and other biological materials through the cover into the basin; and an adhesive member attached to a bottom of the basin to secure the basin to a surgical work surface to minimize tipping of the basin during surgery; and a dual purpose lid means for accommodating blood, fluids, and other biological waste material during a surgical procedure while also being adapted to be secured in a lid configuration to the first biowaste container to retain the materials in the first biowaste container during disposal, the dual purpose lid means including an adhesive member attached to a bottom of the basin to secure the basin to a surgical work surface to minimize tipping of the basin during surgery.

22. The multipart biowaste container of claim 21, wherein the adhesive member comprises an adhesive layer.

23. The multipart biowaste container of claim 21, wherein the adhesive member comprises an adhesive pad.

24. The multipart biowaste container of claim 21, wherein the dual purpose lid means comprises a secondary biowaste container having an absorbent pad.

25. The multipart biowaste container of claim 21, wherein the dual purpose lid means is configured to nest with the first biowaste container during shipping and storage of the multipart biowaste container.

26. The multipart biowaste container of claim 24, wherein the secondary biowaste container includes at least one pour channel.

27. The multipart biowaste container of claim 26, wherein the pour channel is adapted to facilitate transition of fluids from the interior of the secondary biowaste container to the first biowaste container.

28. The multipart biowaste container of claim 26, wherein the pour channel comprises at least one pour spout positioned in a corner of the secondary biowaste container, the pour channel being deeper near the interior of the biowaste container.

29. A multipart biowaste container system comprising:

an anti-splash container comprising a basin adapted to accommodate blood, fluid, and other materials resulting from a surgical procedure;

a dual purpose lid container adapted to accommodate blood, fluid, and other materials resulting from a surgical procedure while also being configured to be secured on the anti-splash container as a lid;

a supplementary container, wherein the anti-splash container, dual purpose lid container; and supplementary container are configured to be secured to one another to provide a substantially fluid tight seal.

30. The multipart biowaste container of claim 29, wherein the anti-splash container includes a splash guard to minimize splashing or spilling of fluids from the anti-splash container.

31. The multipart biowaste container of claim 30, wherein the splash guard includes three input sites to allow the passage of blood, fluids, and other materials into the anti-splash container.

32. The multipart biowaste container of claim 31, wherein the splash guard includes and at least one valve member associated with at least one input site.

33. The multipart biowaste container of claim 32, wherein the at least one valve member comprises a slit valve.

34. The multipart biowaste container of claim 33, wherein the splash guard includes a plurality of valve members associated with at least one input site.

* * * * *